United States Patent [19]

Greenspan

[11] 4,209,485
[45] Jun. 24, 1980

[54] METHOD OF MAKING A VALVE APPARATUS

[76] Inventor: Donald J. Greenspan, 235 Pavilion Ave., Riverside, N.J. 08075

[21] Appl. No.: 909,474

[22] Filed: May 25, 1978

Related U.S. Application Data

[63] Continuation of Ser. No. 793,284, May 3, 1977, abandoned.

[51] Int. Cl.² .................. B29F 1/14; B29D 23/02; B29C 1/06
[52] U.S. Cl. ............................ 264/242; 264/296; 264/318; 264/334; 29/157.1 R; 137/537; 137/852; 222/494; 222/496
[58] Field of Search ............ 29/157.1 R; 264/242, 264/334, 318, 296; 137/852, 843, 529, 537, DIG. 4; 222/496, 497, 494; 401/271-273; 128/274

[56] References Cited

U.S. PATENT DOCUMENTS

| | | | |
|---|---|---|---|
| 3,013,308 | 12/1961 | Armour | 264/318 |
| 3,159,318 | 12/1964 | Green | 29/157.1 R |
| 3,227,173 | 1/1966 | Bernstein | 137/451 |
| 3,340,561 | 9/1967 | Schwartzman | 401/206 |
| 3,344,942 | 10/1967 | Hedgewick | 264/318 |
| 3,402,713 | 9/1968 | Senkowski | 264/334 |
| 3,517,682 | 6/1970 | Smith | 137/846 |
| 3,586,068 | 6/1971 | Nicholson | 222/494 |
| 3,608,574 | 9/1971 | Beaussant | 137/529 |
| 3,799,342 | 3/1974 | Greenspan | 210/DIG. 23 |
| 3,827,439 | 8/1974 | Schulte et al. | 128/274 |
| 3,831,629 | 8/1974 | Mackal et al. | 137/DIG. 4 |
| 3,957,944 | 5/1976 | Guala | 264/334 |
| 3,969,250 | 7/1976 | Farr | 210/DIG. 23 |
| 4,005,101 | 1/1977 | Ruch | 264/318 |
| 4,038,358 | 7/1977 | Wrasman | 264/242 |

FOREIGN PATENT DOCUMENTS

897678  5/1962  United Kingdom ............ 137/852

*Primary Examiner*—Daniel C. Crane
*Attorney, Agent, or Firm*—Woodcock, Washburn, Kurtz, Mackiewicz & Norris

[57] ABSTRACT

A valve apparatus is integrally molded from an elastomeric material so as to form a valve seating portion including a valve opening, a valve member and connective strands extending from the valve seating portion to the valve member. The valve member is initially molded on one side of the valve opening, and a portion of the valve member is passed through the opening to the other side thereof. The connective strands are stretched while passing a portion of the valve member through the opening so as to create a bias on the valve member which tends to seat the valve member on the other side of the opening.

14 Claims, 9 Drawing Figures

U.S. Patent  Jun. 24, 1980  Sheet 1 of 3  4,209,485
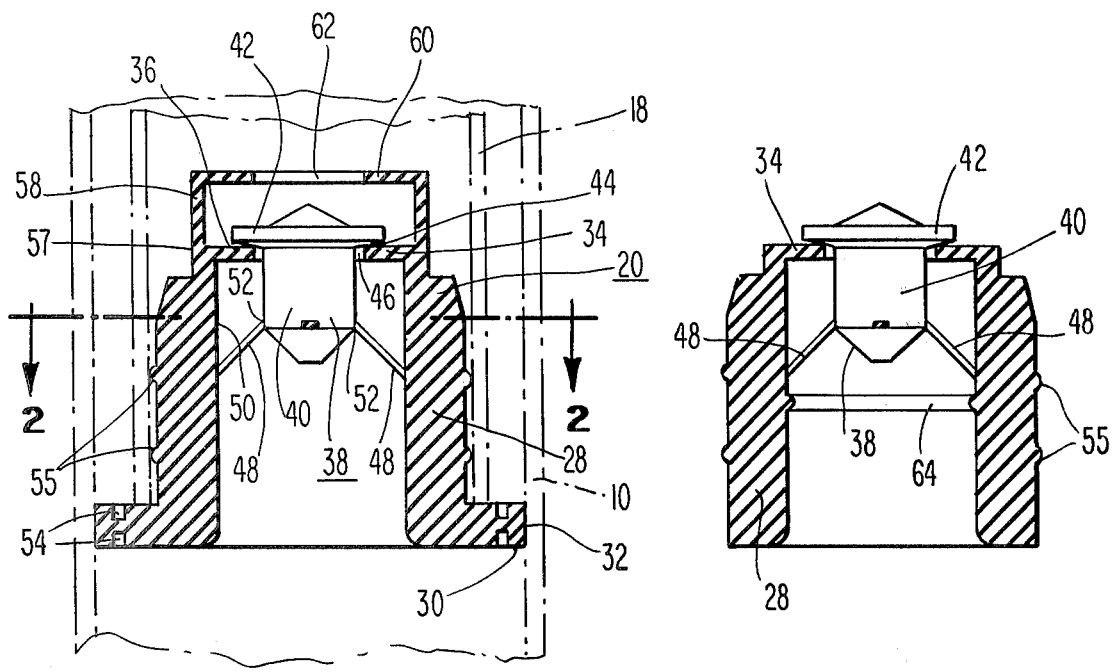
Fig. 1
Fig. 3
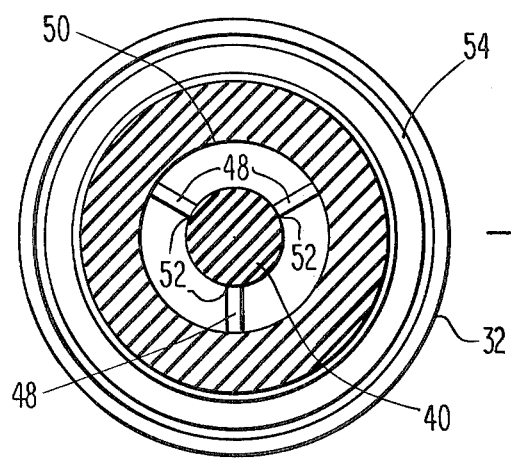
Fig. 2

METHOD OF MAKING A VALVE APPARATUS

This is a continuation, of application Ser. No. 793,284, filed May 3, 1977, now abandoned.

BACKGROUND OF THE INVENTION

The invention relates to a simplified valve apparatus and a method of making such a simplified valve apparatus.

There is a substantial need for relatively low cost valves which may perform a variety of functions in rather small and intricate apparatus. In many applications, such valves must be capable of operating with a high degree of precision, i.e., close at the proper time and open at the proper time. The medical field represents an area in which such valves have a high degree of utility.

One particular application is serum separator tubes which comprise tubular members having one end closed by a plug which is formed from an elastomeric material. Typically, the plug includes a one-way valve which is forced open as the serum separator tube is forced downwardly through a blood sample in a collection tube so as to allow the serum or plasma to flow into the separator tube. When the separator tube becomes stationary relative to the collection tube, i.e., just before contact with the formed elements of the blood, the one-way valve closes so as to isolate the plasma within the separator tube. The separator tube may then be withdrawn.

It has been found to be particularly desirable to utilize the separator tube in and of itself as the transport device for transporting the serum or plasma to the laboratory from the point at which the blood sample is taken. This requires that the one-way valve at the closed end of the separator tube be essentially leak-proof. My U.S. Pat. Nos. 3,661,265 and 3,799,342 disclose a substantially leak-proof valve which does permit the use of a separator tube as a transport device. The one-way valve disclosed therein essentially relies upon the elastomeric properties of the plug to return the valve to the closed condition, i.e., there is no force or bias acting on the valve when the separator tube is in the stationary position and the valve is closed. Rather the valve elements, when properly structured, merely contact one another when returning to a natural or unbiased state in which they were originally molded. Proper closure of these valves may be assisted by the tubular member if the inside diameter of the tubular member is slightly smaller than the outside diameter of the plug but the tolerances on the inside diameter of the tubular member are difficult to control particularly where the tubes are extruded.

U.S. Pat. No. 3,954,614 also discloses a valve and a separator tube which is characterized by little or no seating forces when the valve is in the closed position. The same is true with respect to U.S. Pat. No. 3,962,085 wherein the periphery of a disc acts on a valve which is closed when the disc is in the closed position. However, there are no substantial seating forces beyond the weight of the blood sample itself. Valves such as those shown in U.S. Pat. Nos. 1,777,408 and 2,191,636 are biased so as to provide a substantial sealing force when in the closed position, but such valves are relatively complex.

SUMMARY OF THE INVENTION

It is an object of this invention to provide a simplified valve which will function with precision.

It is a further object of this invention to provide a low-cost method for making such a valve.

In accordance with these and other objects, a valve apparatus representing a preferred embodiment of the invention comprises a valve seating portion including a valve opening, a valve member and connective means extending from the valve seating portion to the valve member. The valve apparatus is integrally molded from an elastomeric material with the valve member on one side of the valve opening and the connective means in the unstretched or untensioned state. Subsequent to molding, at least a portion of the valve member is passed through the valve opening and set on the other side thereof while the connective means stretch so as to create a bias on the valve member through the connective means which tends to seat the valve member on the other side of the valve opening.

In accordance with one important aspect of the invention, the valve member is forced through the valve opening while at least a portion of the valve apparatus is retained by the mold means. In the preferred embodiment of the invention, the mold means comprises a first and second molding means. The valve member is retained by and pulled through the valve opening by the second mold means which partially forms the valve member and the valve seating portion as the second mold means separates from the first mold means which also partially forms the valve member and the valve seating portion. The second mold means may also include means for holding the valve seating portion relatively stationary as the valve member is pulled through the valve opening and the remainder of the second mold means moves relative to the molding means. The remainder of the second mold means may comprise an outer portion for forming the periphery of the valve apparatus, an inner portion for forming the central valve apparatus including a portion of the valve member and a valve opening with the holding means comprising a sleeve between the outer portion and the inner portion.

In further accordance with this invention, the valve opening is outwardly deformed as the connective means is stretched so as to allow at least a head portion of the valve member to pass therethrough. After the head of the valve member passes through the opening, the valve opening assumes the shape achieved during molding.

In the preferred embodiment of the invention, the valve seating portion comprises a central chamber having a flange at one end forming the valve opening and the valve member is molded within the chamber. The connective means may comprise at least one strand which is connected between the head portion and/or the body portion of the valve member. Preferably, the connective means comprises a plurality of strands. The valve apparatus may further comprise another flange which is located adjacent but spaced from the flange including the valve opening such that the head portion is positioned between the other flange and the flange including the valve opening.

BRIEF DESCRIPTION OF THE DRAWINGS

FIG. 1 is a sectional view of a valve apparatus incorporating the invention;

FIG. 2 is a sectional view of the apparatus taken along line 2—2 of FIG. 1;

FIG. 3 is a sectional view of another valve apparatus incorporating the invention;

DETAILED DESCRIPTION OF PREFERRED EMBODIMENTS

Figure 4:
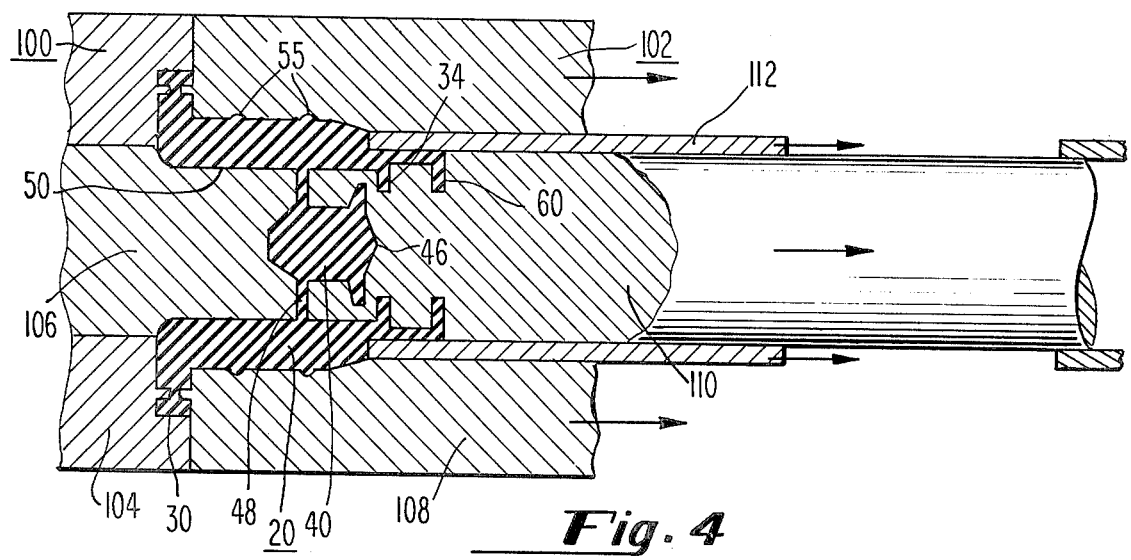
FIG. 4 is a sectional view of a mold in which the valve apparatus of FIG. 1 is molded.

As shown in FIGS. 1 and 2, a plug 20 made in accordance with this invention comprises a valve seating portion including a substantially cylindrical body which is terminated at one end by a flange 30 which is adapted to form a seal between a sealing surface 32 and a tubular member 10 shown in phantom. The other end of the valve seating portion 28 comprises a radially inwardly directed annular flange 34 which is adapted to form a valve seat along the surface 36 for a movable valve member 38. The valve member 38 comprises a body portion 40 terminated by a sealing head portion 42 having a surface 44 which seats on the surface 36 when the sealing portion or head is in the seated position as shown in FIG. 1.

In order to provide a closing bias on the valve member 38 which is independent of the diameter of the inner tubular member 18 which is shown in phantom, connective means in the form of a resilient strand or strut members 48 attached to the interior walls 50 of the valve seating portion 28 of the plug 20. As shown in FIG. 2, three such struts or strands 48 may be utilized which are evenly spaced around the wall 50 and the valve member 38 at points of attachment 52 so as to assure that the appropriate seal will be formed between the sealing surface 44 and the seating surface 36 as shown in FIG. 1.

In accordance with this invention, the integrally molded plug 20 shown in FIGS. 1 and 2 comprises an elastomeric material such as Kraton or rubber. In FIG. 1, the valve member 38 is in the biased or set position with tension on the strands 48. However, as originally molded, there is no bias on the strands 48 since the head 42 and the remainder of the valve 38 is molded on the other side of the valve opening 46 as will be subsequently shown with reference to FIG. 4. When the molding is completed, the head or sealing portion 42 is forced through the opening 46 as shown in FIG. 1 with the strands 48 under sufficient tension and storing sufficient energy so as to force the sealing surface 44 into contact with the seating surface 36. However, the valve member 38 may be forced open by further stretching the strands 48.

As also shown in FIGS. 1 and 2, the flange 30 comprises annular relieved areas 54 located on opposite sides of the flange 30. The relieved areas 54 allow the sealing surface 32 to be extended radially outwardly or retracted radially inwardly so as to accommodate different internal diameters of the tube 10. FIG. 1 also shows annular beads 55 which are adapted to form a seal with the tube 18. By relying on the beads 55 to form the necessary seal, the tolerances on the diameter of the tubular member 18 become less critical. Similarly, an annular recess 57 is provided adjacent the flange 34 so as to preclude contact between the tubular member 18 and the flange 34 which could impair proper operation of the valve.

As also shown in FIG. 1, the plug 20 includes a hood 58 adjacent the valve opening 46 in the head 42. The hood 58 includes a radially inwardly directed flange 60 and a central opening 62. The flange 60 serves to deflect fluid flowing through the opening 46.

In operation, the valve of FIGS. 1 and 2 operates by force of fluid within the chamber formed by the walls 50 acting upwardly against the valve member 38 so as to raise seating surface 44 of the head 42 off the seating surface 36 of the flange 34 around the entire periphery and allow the head 42 to float above the opening 46. In the absence of fluid flow outwardly through the valve opening 46, the seating surface 44 of the head 42 returns to form a seal with the seating surface 36 of the flange 34.

Reference will now be made to FIGS. 4-9 for a description of the manner in which the plug of FIGS. 1 and 2 is molded. As shown in FIG. 4, plug 20 has been molded between a first mold section 100 and a second mold section 102. The first mold section 100 includes an outer portion 104 which partially forms the flange 30 and a central portion 106 which partially forms the walls 50 and a portion of the valve member 38 as well as the strands 48 within the chamber formed by the walls 50.

Figure 5:
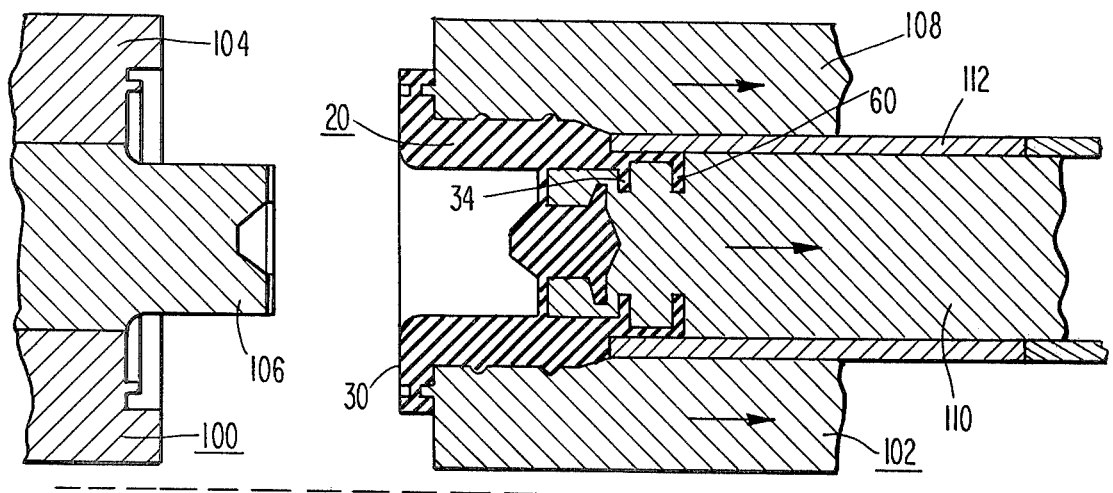
FIG. 5 is a sectional view of the mold of FIG. 4 as the mold begins to open.

The second section 102 of the mold comprises an outer portion 108, an inner or central portion 110 and a sleeve 112 therebetween. The outer portion 108 forms the wall of the plug 20 including the beads 55. The inner or central portion 110 forms the flanges 34 and 60 as well as the valve opening 46. The central portion 110 also forms a substantial portion of the valve member 40 including the head 42 as well as cooperating with the first section 100 of the mold to form the strands 48. After the molding has been completed as depicted by FIG. 4, the mold sections 100 and 102 begin to separate as shown in FIG. 5. As the second section 102 separates from the first section 100, the flange 30 is released from the outer portion 104 of the first section 100 and the inner portion 106 is withdrawn from the interior chamber of the plug 20. The plug 20 remains in place with respect to the outer portion 108, the inner portion 110 and the sleeve 112 of the second mold section 102 which, at this initial stage of release, move as a unit.

Figure 6:
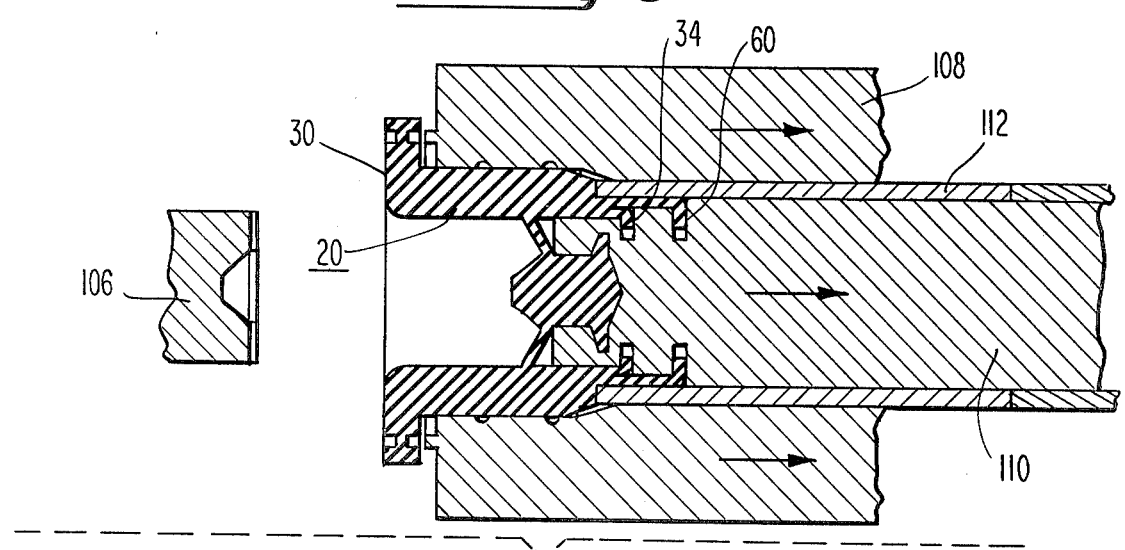
FIG. 6 is a sectional view of the mold of FIG. 4 as the mold continues to open and the setting of the valve begins.

In FIG. 6, the sleeve 112 has become stationary as the outer mold portion 108 and the inner mold portion 110 of the second section 102 continue to move so as to hold the flange 60 and the flange 34 and begin the release of the plug 20 with respect to the second mold section 102. Simultaneously and in accordance with this invention, the setting of the valve member 40 is initiated as the flange 34 which forms the valve opening 46 begins to deform so as to permit passage of the head 46 therethrough.

Figure 7:
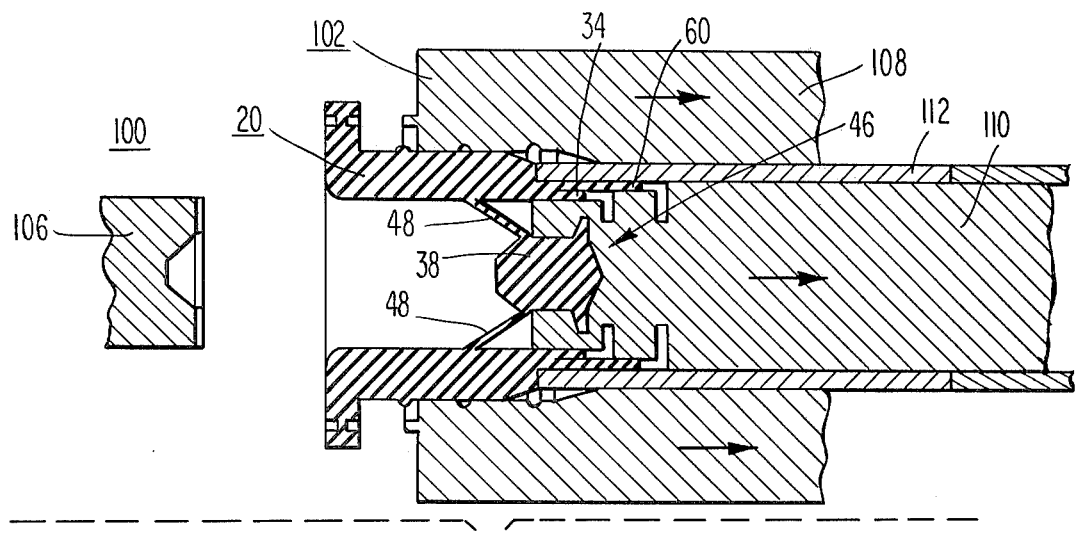
FIG. 7 is a sectional view of the mold of FIG. 4 in a further state of opening with the valve opening deformed so as to permit setting of the valve.

Referring now to FIG. 7, the opening 46 in the flange 34 is now fully deformed as the head 42 of the valve member 38 passes therethrough. This is accomplished by permitting the outer portin 108 and the inner portion 110 of the mold section 102 to continue opening or moving with respect to the valve section 100 while the stationary sleeve 112 holds the flanges 60 and 34. It will be noted that the valve member 38 including the head 42 is fully retained within the mold members 108 and 110 as long as the flange 34 continues to be deformed so as to enlarge the opening 46. It will be further noted that the strands 48 of the connective means are extensively stretched at this stage in the mold opening procedure.

Figure 8:
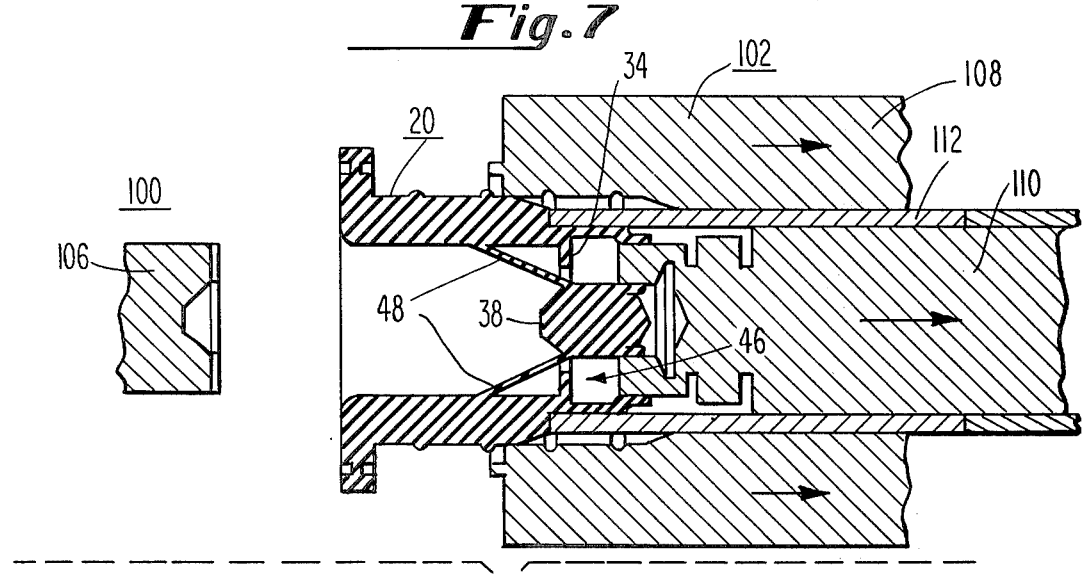
FIG. 8 is a sectional view of the mold of FIG. 4 in a still further state of opening with the mold beginning to release the valve during setting.
Figure 9:
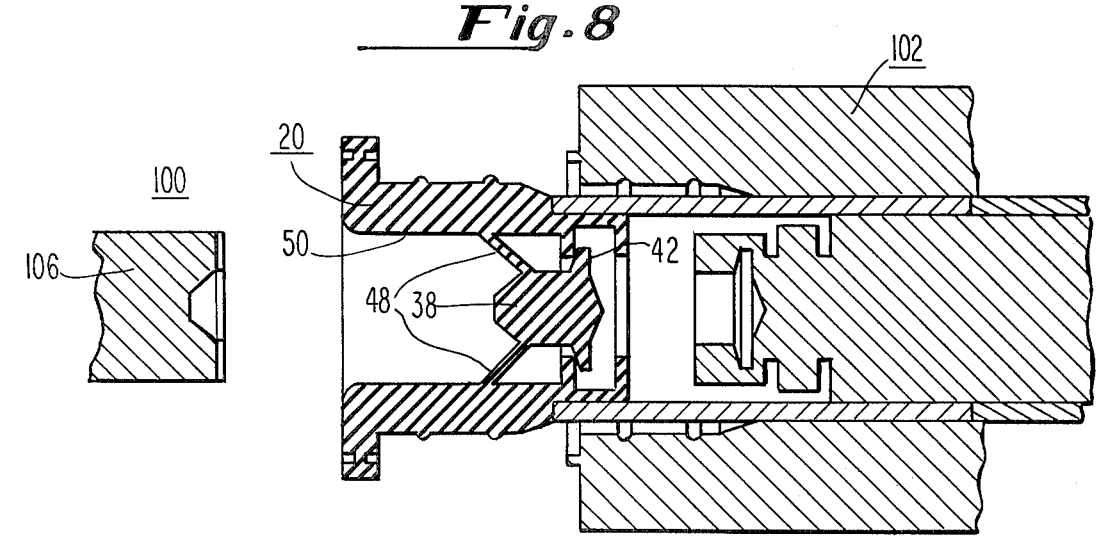
FIG. 9 is a sectional view of the mold of FIG. 4 with the valve apparatus substantially released from the mold and the valve member fully set in the valve opening.

In FIG. 8, as the mold section 102 exclusive of the sleeve 112 continues to move, the strands 48 are stretched to a point so as to provide sufficient force to pull the valve member 38 from the inner portion 110 of the mold section 102. Since the flange 34 has now returned to the original molded state, i.e., undeformed, the head 42 of the valve member 38 will not pass through valve opening 46 when the valve member 38 is fully released from the inner mold portion 110 as shown in FIG. 9.

It will therefore be appreciated that valve member 38 is molded within the chamber formed by the walls 50 of the plug 20. However, prior to removal of the valve from the mold, the valve member 38 with the head 42 is moved from one side of the valve opening to the other side to set the valve. Simultaneously with the setting of the valve, the connective means, i.e., the strands 48, are subjected to stretching so as to ultimately bias the valve member 38 to the closed position.

In FIGS. 1 and 2, the plug 20 is mounted within the end of an inner tube 18 and the flange 30 is adapted to form a seal with an outer tube 10. The tubes 10 and 18 are intended to represent a collection tube and a serum separator tube of the type shown in detail in copending application Ser. No. 793,284 filed May 3, 1977. It will be understood that the plug 20 may take the various forms shown in the aforesaid application which is incorporated herein by reference.

It will also be understood that the plug 20 may be modified to a plunger-type serum separator of the type disclosed in the aforesaid application. For example, the plug may be modified as shown in FIG. 3 so as to eliminate the flange 60 which is intended to deflect the serum or plasma passing through the valve in the aforesaid serum separator application. Furthermore, the flange 30 may be eliminated and comparable structure may be provided by a separate O-ring located on the tube 18. In some instances, it may be desirable to utilize an annular bead 64 on the walls 50 to prevent any filter lodged within the chamber formed by the walls 50 from interfering with the valve member 38. It will be understood that the valve apparatus shown in FIG. 3 may be integrally molded as part of a larger structure.

In the foregoing, a description is provided as to how tension is developed on the strands 48. It will also be understood that the tension on the strands 48 may be relieved by forcing the head 42 back through the opening 46. It will also be understood that the head 42 may be molded in place on the opposite side of the valve opening and then pushed through the opening thereby placing tension on the strands which are appropriately positioned on the wall 50 for this purpose.

As utilized herein, the phrase valve seating portion is not limited to that portion of the structure on which the valve actually seats. Rather, it is that structure associated with the actual seating structure which remains stationary relative to the movement of the valve member.

Although specific embodiments of the invention have been shown and described, it will be understood that other embodiments and modifications may be utilized without departing from the true spirit and scope of the invention as set forth in the appended claims.

What is claimed is:

1. A method of making a valve apparatus comprising a valve seating portion including a valve opening, a valve member and a connective means extending from said valve seating portion to said valve member, said method comprising the following steps:
   integrally molding an elastomeric material to form said valve seating portion, said valve member and said connective means with said valve member on one side of said valve opening;
   passing at least a portion of said valve member through said valve opening to the other side thereof; and
   stretching said connective means while passing said portion of said valve member through said opening so as to create a bias on said valve member which tends to seat said valve member on said other side of said opening.

2. The method of claim 1 wherein said opening is outwardly deformed as said connective means is stretched so as to allow said portion of said valve member to pass therethrough.

3. The method of claim 1 wherein said valve member is forced through said opening while at least a portion of said valve apparatus is retained by mold means.

4. The method of claim 2 wherein said valve apparatus is formed by a first and second mold means, said valve member being retained by and pulled through said opening by said second mold means which partially forms said valve member and said valve seating portion as said second mold means separates from said first mold means which also partially forms said valve member and said valve seating portion.

5. The method of claim 4 wherein said second mold means includes means for holding said valve seating portion relatively stationary as said valve member is pulled through said valve opening and the remainder of said second mold means moves relative to said first mold means.

6. The method of claim 5 wherein said second mold means comprises an outer portion for forming the periphery of the valve structure, an inner mold means for forming the central valve apparatus including a portion of said valve member and said valve opening, said holding means comprises a sleeve between said outer portion and said central portion.

7. The method of claim 4 wherein said opening is deformed as said second mold means separates from said valve seating portion and subsequently assumes the shape of said opening during molding after said valve member has passed therethrough while being retained by said second mold means.

8. The method of claim 7 wherein said connective means is stretched as said first mold means and said second mold means separate and said valve member is retained by said second mold means until said opening assumes said shape during molding after being deformed during the separation of said first mold means and said second mold means.

9. The method of claim 8 wherein said connective means retracts when said valve member is released from said second mold means to a lesser stretched condition with said valve member seated on the other side of said opening.

10. The method of claim 9 wherein said connective means comprises a plurality of strands and said first mold means and said second mold means at least partially form said connective means which stretch as said first mold means and said second mold means separate.

11. The method of claim 1 wherein said valve seating portion includes a central chamber having a flange at one end forming said opening, said valve member being molded within said chamber.

12. The method of claim 11 wherein said valve member comprises a head portion, said head portion passing through said opening before seating on said other side of said opening.

13. The method of claim 11 wherein said connective means comprises a plurality of strands extending from the central chamber to said valve member, said strands being stretched as said portion of said valve member passes through said opening.

14. The method of claim 1 wherein said valve seating portion includes a central chamber having a flange at said one end forming said valve opening, said valve apparatus comprising another flange having another opening spaced from said valve opening on said other side, said valve member being molded within said chamber and with at least said portion being passed through said valve opening without being passed through said other opening.

* * * * *